United States Patent
Hui et al.

(10) Patent No.: US 7,794,970 B2
(45) Date of Patent: Sep. 14, 2010

(54) METHOD FOR GENERATING F(AB')2 ANTIBODY FRAGMENTS

(75) Inventors: John O. Hui, Newbury Park, CA (US); Mitsuru Haniu, Thousand Oaks, CA (US); Hsieng Sen Lu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 687 days.

(21) Appl. No.: 11/522,577

(22) Filed: Sep. 18, 2006

(65) Prior Publication Data

US 2007/0154471 A1  Jul. 5, 2007

Related U.S. Application Data

(60) Provisional application No. 60/718,883, filed on Sep. 20, 2005.

(51) Int. Cl.
*C07K 16/00* (2006.01)
*C12N 21/06* (2006.01)

(52) U.S. Cl. .................. 435/68.1; 424/809; 436/512; 530/412; 530/413; 530/416; 530/866

(58) Field of Classification Search .......... None
See application file for complete search history.

(56) References Cited

U.S. PATENT DOCUMENTS 4,344,938 A * 8/1982 Sedlacek et al. ......... 424/130.1
4,849,352 A   7/1989 Sullivan
4,925,662 A   5/1990 Oguchi
5,576,184 A * 11/1996 Better et al. ............. 435/7.23
2002/0058324 A1  5/2002 Blank

FOREIGN PATENT DOCUMENTS

JP     51-95125 A * 8/1975
JP     2004041143    2/2004

OTHER PUBLICATIONS

JP,2004-041143,A [Claim + Detailed Description], Machine Translation thereof.*
Lin et al., J. Biol. Chem. 244, 789-793, 1969.*
Translation of JP 51095125 A (Matsuzawa), USPTO May 2009.*
Page et al, Methods in Molecular Biology, vol. 32, 407-431, 1994.*
Galloway D.R., et al., "*Pseudomonas aeruginosa* Elastase and Elastolysis Revisted: Recent Developments," Molecular Microbiology, vol. 5, No. 10, pp. 2315-2321, (Oct. 1991).
International Search Report.
Sigma-Aldrich, Inc. Product Information Sheet for Product T7902.
Yu-Sheng Victor Liu, et al., Primary Structure of a Human IGA1 Immunoglobulin, J. Biological Chem., 254(8), 2859-2864 (1979).

* cited by examiner

*Primary Examiner*—David A. Saunders
(74) *Attorney, Agent, or Firm*—John A. Lamerdin (57) ABSTRACT

Methods for generating $F(ab')_2$ fragments from antibodies using thermolysin as well as $F(ab')_2$ fragments and compositions comprising $F(ab')_2$ fragments generated by the method are described.

6 Claims, 5 Drawing Sheets

METHOD FOR GENERATING F(AB')2 ANTIBODY FRAGMENTS

FIELD OF INVENTION

The invention relates to methods for generating F(ab')$_2$ antibody fragments, and pharmaceutical compositions comprising F(ab')$_2$ antibody fragments generated by the methods. More particularly, the invention relates to methods for generating F(ab')$_2$ antibody fragments using limited thermolysin digestion of antibodies.

BACKGROUND

Antibodies are blood serum proteins, sometimes called immunoglobulins, which are generated by the immune system in response to a foreign substance or organism (antigens). Antibodies are characterized by specific binding with their particular antigen, neutralizing them so that they are removed from the circulation. Antibody technology is widely used for the diagnosis, monitoring, prevention and treatment of many different ailments.

Several types of immunoglobulins (Ig) have been identified, such as, IgG, IgM, IgD, IgA and IgE. The majority of commercially produced immunoglobulins are the IgG-type, because they constitute a large amount of the Ig in blood serum and are associated with a mature immune response. While all IgGs have the same general structure, they fall into different isotype categories, such as IgG1, IgG2, IgG3, and IgG4. IgGs are composed of four polypeptide chains, two that are heavy (H) and two light (L). Each heavy chain is linked to a light chain via a disulfide bond and the two heavy chains, in turn, are joined together by disulfide bridges at a region known as the hinge. Each heavy chain has three constant regions, $C_{H1}$, $C_{H2}$, and $C_{H3}$, the last two in the carboxy terminal region (after the hinge) and the first in the amino terminal region (immediately before the hinge) and a Variable region ($V_H$) in the amino terminal end, while each light chain has only one constant region, $C_L$, in the carboxy terminal end and one variable region, $V_L$, in the amino terminal end.

Enzymatic digestion of IgG can result in a number of different fragments, depending on the enzyme used. Papain and pepsin are among the most common enzymes used to digest IgGs. Papain typically generates three fragments, the crystallizing fragment (Fc) and two antigen-binding fragments (Fab). Pepsin typically generates one F(ab')$_2$ fragment and completely digests the Fc fragment. Fab and F(ab')$_2$ fragments can retain the capacity for specific binding to their specific antigen. F(ab')$_2$ also precipitates its specific antigen. The other antibody fraction, Fc, typically acts as a marker signal for macrophages and the activation of lymphocytes for the recognition and phagocytosis of the antigen-antibody complex.

The Fc fragment comprises the antigenic determinants of the antibody in such a way that, when a patient is administered whole antibodies generated in, e.g., an animal of another species, the patient may generate an immune response against these antigenic determinants. This can give rise to varied adverse secondary responses, including anaphylactic shock. These problems can be reduced by digesting the antibodies with enzymes such as papain or pepsin. These enzymes can generate Fab, F(ab')$_2$, and Fc fractions that can be isolated and purified, and allow for administration of Fab or F(ab')$_2$ fragments to a subject.

The F(ab')$_2$ fragment has a particular advantage over Fab in that it is retained in the organism for a longer period because of its molecular weight. Moreover, F(ab')$_2$ retains the capacity to precipitate its antigen under physiological conditions. As the F(ab')$_2$ fragment retains the specific binding character of the intact antibody, its utility is similar to the intact antibody. However because the F(ab')$_2$ fragment lacks the Fc fragment, it is less likely to be recognized as foreign by the recipient, thus providing greater tolerance to application and reducing the possibility of secondary reactions, which is particularly useful for prolonged treatments such as those applied in autoimmune diseases.

Many methods for the production of antibodies and their fragments are known. For example, in U.S. Pat. No. 4,849,352, Sullivan et al. describes the production of Fab fragments through the digestion of antibodies with papain immobilized in polyacrylamide, and F(ab')$_2$ fragments through the digestion of antibodies with immobilized pepsin. A number of these methods for the production of antibody fragments such as F(ab')$_2$, by means of digestion of whole antibodies with pepsin have shown several disadvantages, such as considerable loss of biological activity, a high residual content of whole antibodies and other impurities, and digestion of the F(ab')$_2$ fragment itself. Thus, straightforward methods are needed that allow for the production of F(ab')$_2$ fragments from whole antibodies and antibodies that comprise sequence in addition to the F(ab')$_2$ region, which methods provide high fragment yields and retains the binding activity of the intact antibody.

SUMMARY OF THE INVENTION

One aspect of the invention relates to a method for generating F(ab')$_2$ fragments comprising contacting one or more antibodies, or a solution comprising one or more antibodies with thermolysin under conditions that allow for limited enzymatic digestion; and separating and purifying the F(ab')$_2$ molecules generated by the limited digestion from the remaining antibody fragments.

In one aspect, the invention relates to F(ab')$_2$ fragments produced by the above method.

In another aspect, the invention relates to a F(ab')$_2$ antibody fragment produced by the above method, wherein the fragment is covalently linked to another chemical group.

Another aspect of the present invention relates to a composition comprising an F(ab')$_2$ antibody fragment in combination with an effective amount of a pharmaceutically acceptable carrier.

Other aspects of the present invention will be apparent to one of ordinary skill on consideration of the present disclosure.

DETAILED DESCRIPTION OF THE INVENTION

It is to be understood that both the foregoing general description and the following detailed description are illustrative and are not restrictive of the invention, as claimed. As used here, the use of the singular includes the plural unless specifically stated otherwise, and the use of "or" means "and/or" unless stated otherwise. Furthermore, the use of the terms "having" and "including", as well as other forms, for example, "includes" and "included", are not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, the terms "acidic" or "acidic solution" means that the pH of a solution has a value of less than about seven (7.0). For purposes of this invention, the buffer solution can be made acidic using any type of organic or inorganic acid, so long as it does not generate insoluble complexes with other buffer components, or exceeds the buffering capacity of the buffer system. Those of skill in the art are familiar with the typical buffer systems that are effective at acidic pH ranges (e.g., acetate, citrate, phosphate, succinate, MES, etc.).

The term "antibody" or "antibody fragment" refers to an intact antibody, or a binding fragment thereof that incorporates the entire F(ab')$_2$ fragment, with at least a portion of a non-F(ab')$_2$ region, that can compete with the intact antibody for specific binding. In one embodiment, antibodies or binding fragments thereof are produced by recombinant DNA techniques. In another embodiment the antibodies or binding fragments thereof can be isolated from a natural source. In even other embodiments, the antibodies or binding fragments thereof can be purchased. In certain embodiments, binding fragments can be produced by enzymatic or chemical cleavage of intact antibodies.

The term "polyclonal antibody" refers to a heterogeneous mixture of antibodies that bind to different epitopes of the same antigen. As is well known in the art, polyclonal antibodies can be produced in animals (e.g., rabbits or mice) by means of multiple subcutaneous or intraperitoneal injections of an antigen and an adjuvant. It may be useful to conjugate a target antigen to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for titer.

The term "monoclonal antibody" refers to a collection of antibodies encoded by the same nucleic acid molecule. In certain embodiments, monoclonal antibodies are produced by a single hybridoma or other cell line, or by a transgenic mammal. Examples of suitable methods for preparing monoclonal antibodies are known to those of skill in the art, and include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Monoclonal antibodies typically recognize the same epitope on an antigen. It will be appreciated that the term "monoclonal" is not limited to any particular method for making an antibody.

In one aspect, the invention relates to a method for generating a F(ab')$_2$ fragment from an antibody comprising contacting a solution comprising an antibody with thermolysin, under conditions that allow for limited enzymatic digestion by thermolysin; and optionally separating and purifying the F(ab')$_2$ molecules generated by the method from the remaining antibody fragments.

In certain embodiments of this aspect, the solution comprising the antibody is acidic, for example, having a pH range from about 2.0 to about 6.9, preferably from about 3.0 to about 6.0. Those skilled in the art will recognize that any buffer system that has buffering capacity in such a pH range can be used. Such buffer systems are well known in the art, and include non-limiting examples such as acetate, citrate, phosphate, 2-morpholinoethanesulfonic acid (MES), and the like.

In other embodiments of this aspect, the contacting of the solution with thermolysin is performed at an elevated temperature, for example, from about just above room temperature (~23° C.) to about 65° C., and preferably from about 40° C. to about 60° C. While the temperature of the contacting step can be adjusted to influence the rate of F(ab')$_2$ fragment formation, it is most preferable to complete the digestion rapidly, to avoid the deleterious effects that can be caused by heat (e.g., thermolysin inactivation, antibody precipitation, pH variation, etc.). Thus, a preferred temperature is about 55° C.

The separating and/or purifying step of the invention can be performed using any well known method in the art, such as affinity chromatography, reverse-phase chromatography, chromatography employing antigen-derivatized media; fractional salt precipitation, and ultrafiltration using membranes having a particular molecular weight exclusion.

In another embodiment of this aspect, the invention provides for the production of F(ab')$_2$ antibody fragments, substantially free of other molecules such as albumin, whole antibodies, and pyrogens, from a source of antibodies such as serum, plasma or the blood of some animal which has been subjected to an immunization scheme with an immunogen, stimulating the generation of specific antibodies against the immunogen. In a preferred embodiment the source antibodies are produced through recombinant DNA technology or are purchased in a purified form.

Any antibody can be used in accordance with the invention, as long as it contains a portion of a non-F(ab')$_2$ region in addition to a complete F(ab')$_2$ region. The antibodies can be non-human, chimeric, humanized, or human antibodies. Preferably, the antibody is a whole antibody, particularly of the immunoglobulin type, preferably IgG, and more preferably IgG1 or IgG2. Suitable antibodies that can be used with the invention include, but are not limited to, Anti_EGFr antibodies (e.g., panitumamab, Erbitux (cetuximab), matuzumab, IMC-11F8, TheraCIM hR3), denosumab, Avastin (bevacizumab), Anti-HGF antibodies, Humira (adalimumab), Anti-Ang-2 antibodies, Herceptin (trastuzumab), Remicade (infliximab), Anti-CD20 antibodies, rituximab, Synagis (palivizumab), Mylotarg (gemtuzumab oxogamicin), Raptiva (efalizumab), Tysabri (natalizumab), Zenapax (daclixumab), NeutroSpec (Technetium ($^{99m}$Tc) fanolesomab), tocilizumab, ProstaScint (Indium-111 labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

The amount of thermolysin effective to generate F(ab')$_2$ fragments can be determined by those of skill in the art. The effective amount will vary and depend on such factors as the amount of antibody to be digested, the temperature of the digestion reaction, and the activity of the thermolysin (i.e., in particular buffers, purity and age of the enzyme, etc.).

In a further aspect, the invention relates to F(ab')$_2$ fragments that are generated by the above-described method. The F(ab')$_2$ fragments can be isolated, purified, and stored using any method known in the art. The F(ab')$_2$ fragments retain the specific binding activity of the intact antibody, and can be used for any application that employs the intact antibody (e.g., therapeutics, diagnostic assays, competitive binding assays, etc.).

In another aspect, the invention provides for a F(ab')$_2$ fragment generated by the above-described method, further comprising a half-life extending vehicle, such as those known to those skilled in the art. Such vehicles include, but are not limited to, linear polymers (e.g., polyethylene glycol (PEG), polylysine, dextran, etc.); branched-chain polymers (See, e.g., U.S. Pat. No. 4,289,872 to Denkenwalter et al.; U.S. Pat. No. 5,229,490 to Tam; WO 93/21259 by Frechet et al., published Oct. 28, 1993); a lipid; a cholesterol group (such as a steroid); a carbohydrate or oligosaccharide; or any natural or synthetic protein, polypeptide or peptide that binds to a salvage receptor. Additionally, it will be appreciated that one or more Fc regions from an antibody other than that subjected to thermolysin digestion, can also be employed in accordance with the invention to increase half-life. It will be appreciated that the vehicle can be linked to the F(ab')$_2$ by way of various techniques known in the art including, for example, covalent linkage.

It will be appreciated that the F(ab')$_2$ fragments produced by the described methods can be used as a single therapeutic agent, optionally linked with a vehicle or carrier, and can further be conjugated or otherwise combined with other active agents useful in targeted therapy.

The F(ab')$_2$ generated by the invention may also be used in co-therapies with any other therapeutic agents, including, for example, anti-cancer agents, such as chemotherapeutic agents (such as doxorubicin, 5-FU, folfox, cisplatin, etc.) and other anti cancer agents such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar. Additional examples of co-therapies include Anti-EGFr antibodies (e.g., panitumamab, Erbitux (cetuximab), matuzumab, IMC-11F8, TheraCIM hR3), Denosumab, Avastin (bevacizumab), Anti-HGF antibodies, Humira (adalimumab), Anti-Ang-2 antibodies, Herceptin (trastuzumab), Remicade (infliximab), Anti-CD20 antibodies, rituximab, Synagis (palivizumab), Mylotarg (gemtuzumab oxogamicin), Raptiva (efalizumab), Tysabri (natalizumab), Zenapax (dacliximab), NeutroSpec (Technetium ($^{99m}$Tc) fanolesomab), tocilizumab, ProstaScint (Indium-111 labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

In another aspect, the invention relates to a composition comprising at least one F(ab')$_2$ antibody fragment that is generated by the above-described method, in combination with a pharmaceutically acceptable salt, diluent, vehicle, or carrier.

In certain embodiments, the composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextri-n); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18.sup.th Edition, A. R. Gennaro, ed., Mack Publishing Company (1990). The amount of vehicle or carrier employed in conjunction with the F(ab')$_2$ fragments can be adjusted to provide practical quantity of material per unit dose of composition.

Pharmaceutically acceptable carriers for systemic administration that may be incorporated in the composition of the invention include sugar, acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications, cellulose, vegetable oils, buffers, polyols and alginic acid. Specific pharmaceutically acceptable carriers are described in the following documents, all incorporated herein by reference: U.S. Pat. No. 4,401,663, Buckwalter et al. issued Aug. 30, 1983; European Patent Application No. 089710, LaHann et al. published Sep. 28, 1983; and European Patent Application No. 0068592, Buckwalter et al. published Jan. 5, 1983. Preferred carriers for parenteral administration include propylene glycol, pyrrolidone, ethyl oleate, aqueous ethanol, PEG, albumin, transferrin and combinations thereof. Typically, suitable ranges vary from about 0.5% to about 1%.

In certain embodiments, the pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

Additional pharmaceutical compositions will be evident to those skilled in the art, including formulations comprising other agents, with or without at least one additional therapeutic agents, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058,481), copolymers of L-glutamic acid and gamma ethyl-L-glutamate (Sidman et al., *Biopolymers*, 22:547-556 (1983)), poly (2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra) or poly-D(–)-3-hydroxybutyric acid (EP 133,988). In certain embodiments, sustained release compositions may also include liposomes, which can be prepared by any of several methods known in the art. See, e.g., Eppstein et al., *Proc. Nat. Acad. Sci. USA*, 82:3688-3692 (1985); EP 036, 676; EP 088,046 and EP 143,949.

In order to illustrate better the invention, the following specific examples are provided to illustrate particular aspects of the invention. Because of the illustrative nature of these particular examples they should not be construed as limiting the invention, which is defined in the appended claims.

EXAMPLES

Example 1

Limited Thermolysin Digestion of Antibody 123

Purified Antibody 123 (200 µg) was added to 100 µL of 0.1 M sodium acetate (pH 4.6) containing 1 mM CaCl$_2$. To this sample was added 2 µg of thermolysin (59 U/mg; from *B. thermoproteolyticus rokko*; Sigma, St. Louis, Mo.). The mixture was incubated at 55° C., and was allowed to react for 90 minutes. After 90 minutes, the reaction was frozen, reserving a sample for immediate analysis by reverse-phase high performance liquid chromatography (HPLC).

The digestion products containing the F(ab')$_2$ fragment from the digestion were applied to an ion exchange column (HiTrap SP FF, Amersham Biosciences, Piscataway, N.J.). The F(ab')$_2$ fragment was eluted off the column using a linear sodium chloride gradient, from 50 mM sodium acetate, pH 5.0 to 50 mM sodium acetate containing 1 M sodium chloride, pH 5.0. The fractions containing the F(ab')$_2$ fragment were pooled, concentrated, and applied to a Protein A affinity column to remove any residual intact antibody or Fc fragment.

Figure 1:
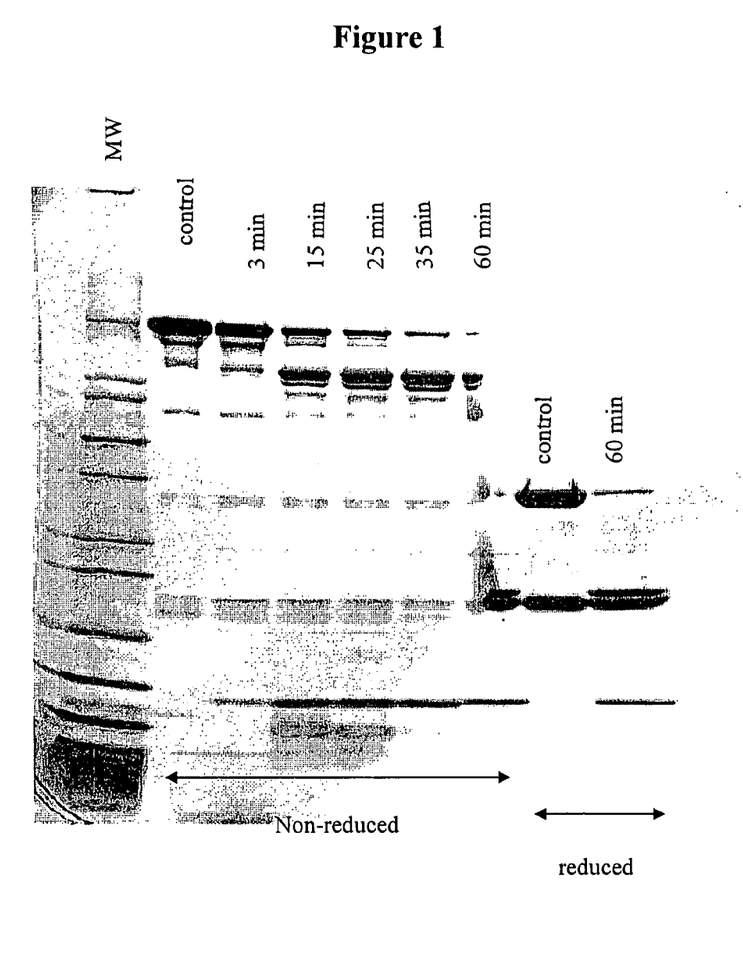
FIG. 1 depicts SDS-PAGE analysis of thermolytic digestion of Antibody 123 as a function of time.
Figure 2:
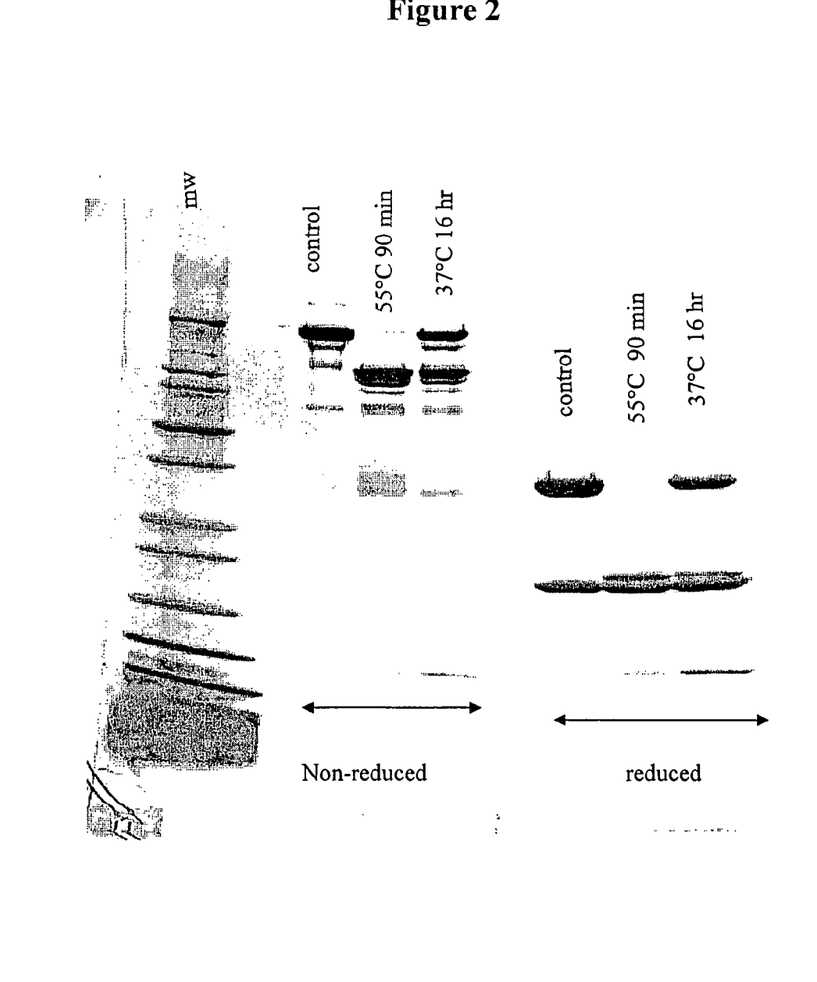
FIG. 2 depicts SDS-PAGE analysis of thermolytic digestion of Antibody 123 as a function of temperature.

The analysis shows that more than 90% of the digestion was complete by 60 minutes (FIG. 1). The behavior of the non-reduced 60 minute lane was caused by diffusion of the reducing agent across the gel. Temperature appears to have an effect on the rate of digestion. FIG. 2 shows that after 90 minutes at 55° C. the digestion was essentially complete, while after 16 hours at 37° C., the digestion was only about 50% complete.

Figure 3:
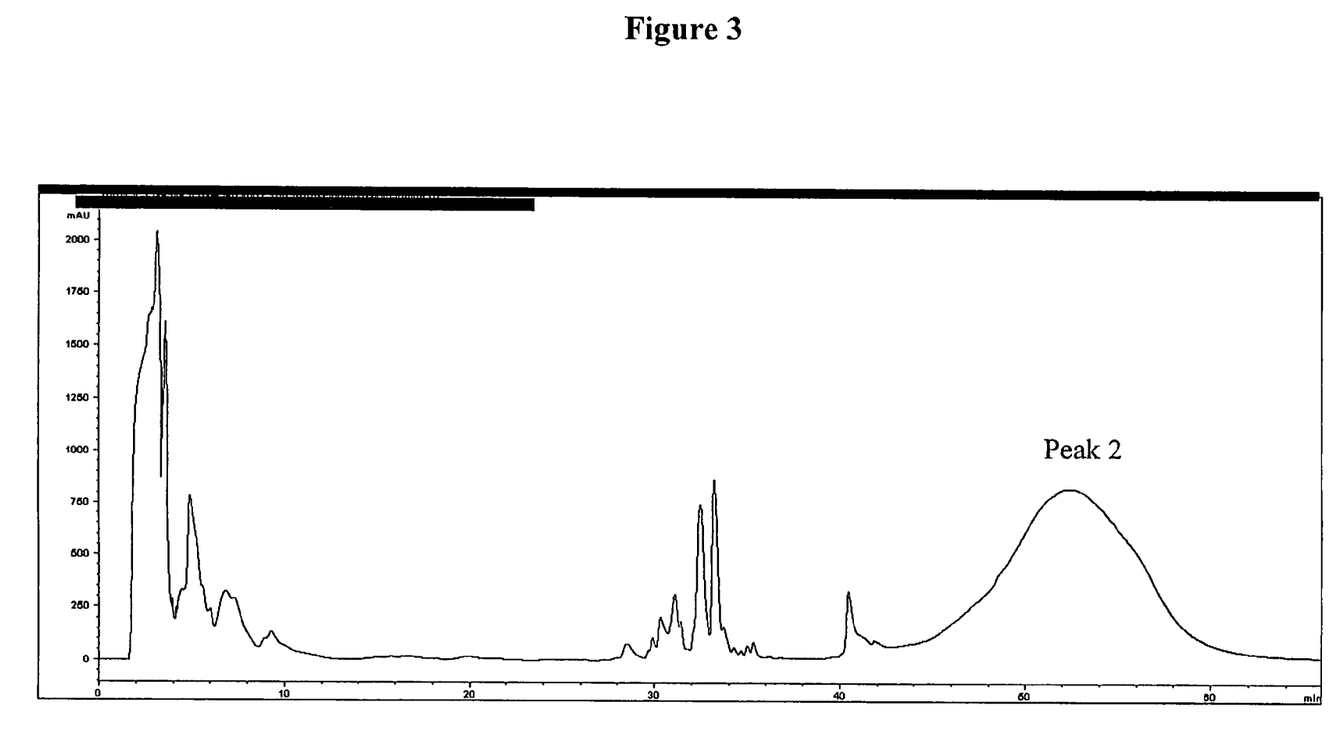
FIG. 3 depicts reverse-phase HPLC analysis of a thermolytic digest of Antibody 123. The broad peak, labeled as peak 2, is the F(ab')$_2$ fragment generated from Antibody 123.
Figure 4:
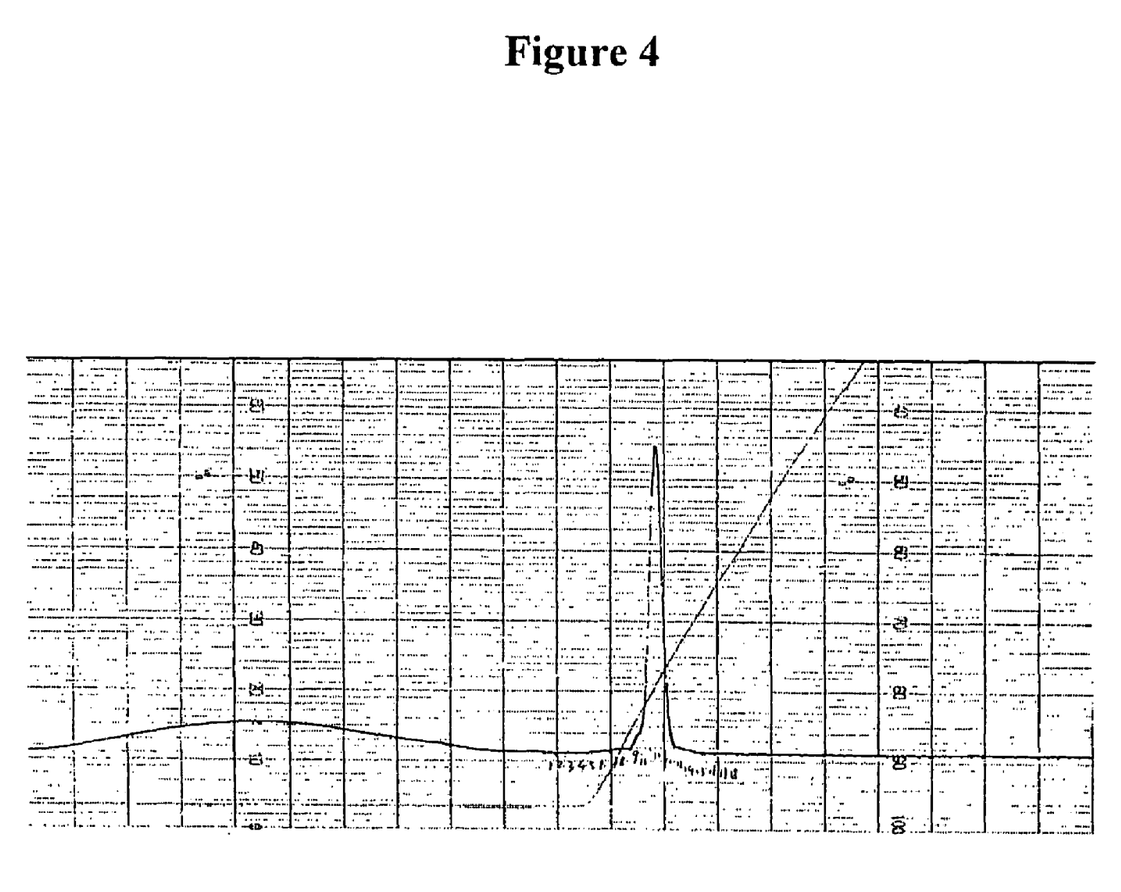
FIG. 4 depicts ion-exchange chromatography (Hi-trap SP) purification profile of (Fab')$_2$ after thermolytic digestion of Antibody 123.

The results further demonstrate that the F(ab')$_2$ fragments were recoverable in high yield after standard chromatographic purification steps, and that the non-F(ab')$_2$ portion (e.g., the Fc portion) is degraded by thermolysin (FIGS. 3-4).

Example 2

Biological Activity of F(ab')$_2$ Fragments Generated from Antibody 123

Figure 5:
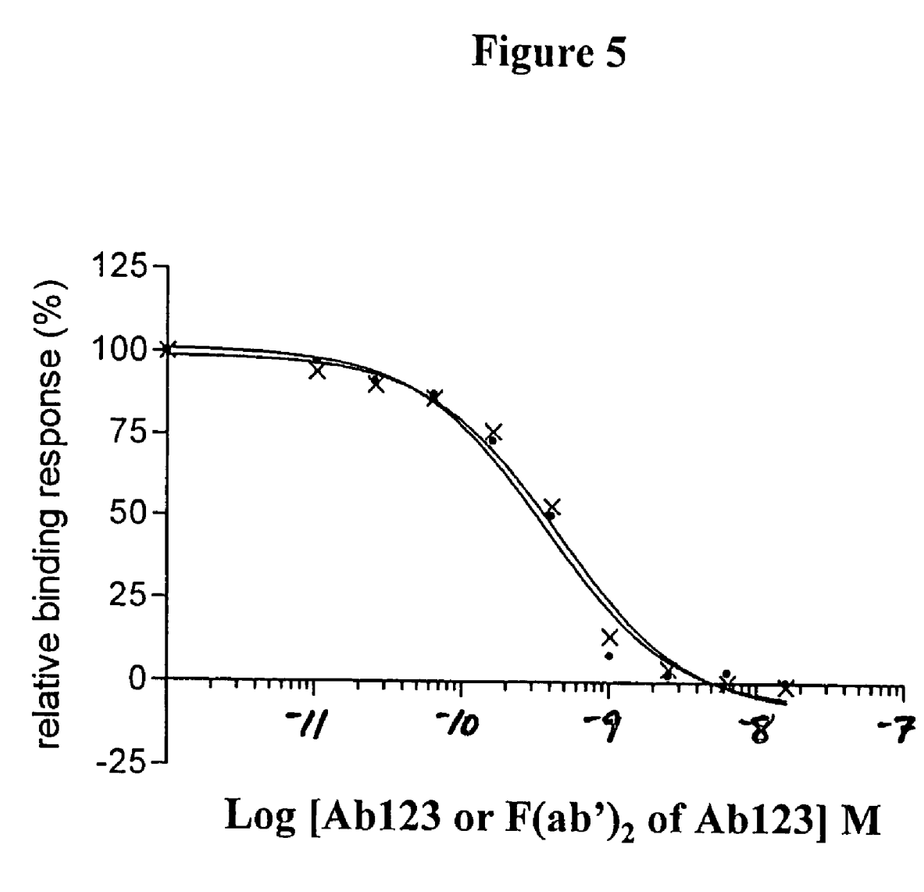
FIG. 5 Binding activity assay of (Fab)$_2$ fragments ("x") generated from Antibody 123 is similar compared to intact Antibody 123 ("○"). EC$_{50}$ values were as shown.

A competitive binding assay between the F(ab')$_2$ fragments generated and isolated in Example 1, and intact Antibody 123 was performed in order to assess specific binding activity of the F(ab')$_2$ fragment. The ligand, L, binds to intact Antibody 123 as well as to the receptor activator of NF-kB (RANK). The binding activity of intact Antibody 123 and the F(ab')$_2$ fragments from Example 1 were measured against immobilized RANK. The results of the binding assay are presented in FIG. 5, which shows identical binding activity between the intact Antibody 123 and the F(ab')$_2$ fragment generated from Antibody 123, in Example 1.

We claim:

1. A method of separating an F(ab')$_2$ fragment of an antibody from a non-F(ab')$_2$ portion of an antibody comprising:
   (a) contacting at least one antibody with thermolysin, under a temperature condition of about 42° C. to about 65° C. and a pH condition selected from the group consisting of:
      (i) about 4.0 to about 5.5; and
      (ii) about 4.0 to about 5.0; and
   (b) isolating the F(ab')$_2$ fragment generated in step (a) from the non-F(ab')$_2$ portion.

2. The method of claim 1, wherein the antibody is an immunoglobulin.

3. The method of claim 2, wherein the immunoglobulin is an IgG.

4. The method of claim 3, wherein the IgG is IgG1 or IgG2.

5. The method of claim 1, wherein the temperature condition of step (a) is from about 50° C. to about 65° C.

6. The method of claim 1, wherein the temperature condition of step (a) is about 55° C.

* * * * *